Figure 1:
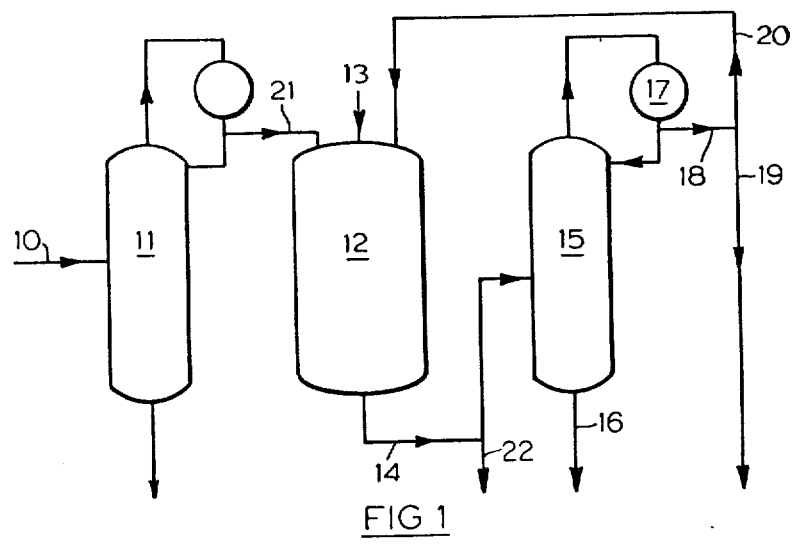

United States Patent [19]

Chase et al.

[11] 4,193,770

[45] Mar. 18, 1980

[54] PREPARATION OF GASOLINE CONTAINING TERTIARYAMYL METHYL ETHER

[75] Inventors: John D. Chase, Oakville; Hanbury J. Woods, Campbellville; Bruce W. Kennedy, Toronto, all of Canada

[73] Assignee: Gulf Canada Limited, Toronto, Canada

[21] Appl. No.: 905,903

[22] Filed: May 15, 1978

Related U.S. Application Data

[63] Continuation-in-part of Ser. No. 863,499, Dec. 22, 1977, abandoned.

[51] Int. Cl.$^2$ .............................................. C10L 1/18
[52] U.S. Cl. ......................................... 44/56; 44/53; 44/77; 568/697
[58] Field of Search ............................... 44/56, 53, 77; 260/614 A

[56] References Cited

U.S. PATENT DOCUMENTS

| | | | |
|---|---|---|---|
| 3,121,124 | 2/1964 | Veidol | 260/614 A |
| 3,482,952 | 12/1969 | Sieg et al. | 44/56 |

FOREIGN PATENT DOCUMENTS 1176620  7/1968  United Kingdom ..................... 568/697

Primary Examiner—Winston A. Douglas
Assistant Examiner—Jacqueline V. Howard
Attorney, Agent, or Firm—D. R. Morrison

[57] ABSTRACT

A process for preparing, from tertiary olefin containing hydrocarbon fractions, a hydrocarbon fraction containing tertiaryamyl methyl ether, the process achieving high conversion of 2-methyl butenes to the ether by etherification with methanol after adequate separation of the 2-methyl butenes from other tertiary olefins, the improved conversion being achieved by separating unreacted 2-methyl butenes from etherified material and recycling them for further reaction.

16 Claims, 2 Drawing Figures

PREPARATION OF GASOLINE CONTAINING TERTIARYAMYL METHYL ETHER

This application is a continuation-in-part of our earlier application Ser. No. 863,499 filed Dec. 22, 1977, now abandoned.

This invention relates to a process for preparing gasoline containing a particular ether and more particularly to an improvement in the preparation of the ether component from a particular portion in raw cracked gasoline fractions, which portion first is effectively separated from lower and higher boiling material, etherified, then blended into gasoline.

It is well known in the art of preparing gasolines for internal combustion engines that various dialkyl ethers can be used to improve the octane ratings of the gasolines. It is also known in the art that volatile olefinic hydrocarbons particularly present in cracked gasoline fractions, especially those olefins containing from four to six carbon atoms, are precursors of atmospheric smog and advantageously are converted to ethers or other materials which are not smog precursors. Branched chain olefinic hydrocarbons having four to six carbon atoms are readily etherified with lower primary alcohols, especially methanol, in contact with etherification catalysts, and four and five carbon olefins are readily and commonly converted to saturated hydrocarbons by alkylation to form alkylate gasoline fractions. However, the processes for etherifying the branched chain olefins, as taught in the art to date, have failed to achieve the optimum of octane improvement available for blended gasolines from olefinic gasoline fractions.

The two major sources of branched chain olefins to make ethers for inclusion in blended gasolines (gasoline pools) are the light catalytically cracked gasoline fraction (LCCG) from gas oil cracking operations and the partially hydrogenated pyrolysis gasoline fraction (HPGB) or "dripolene" from steam cracking of naphtha or heavier distillate fractions. In the prior art of converting these branched chain olefins (specifically tertiary olefins) to ethers for inclusion in gasoline pools, it has been the general practice to etherify the maximum possible proportion of the tertiary olefins with the minimum amount of processing, for example, by etherifying in the presence of excess primary alcohol and/or by etherifying the tertiary olefins in admixture with one another as well as with all the other hydrocarbons occurring in olefinic LCCG or HPGB gasoline fractions. The results have been less than satisfactory, primarily because of the problems involved in separating, from the etherifying reaction effluent, any material which does not beneficially go directly into a gasoline pool or blending tank. Some art also discloses or suggests substantial separation of branched chain olefins of differing number of carbon atoms from one another, prior to etherification, in order to minimize the subsequent separation problems, but the art has apparently always considered that the etherifications should be carried out in substantially the same manner regardless of which tertiary olefin is to be etherified.

It has now been found that the four and five carbon tertiary olefin content of effluents from hydrocarbon cracking operations are more beneficially etherified for octane improvement of blended gasoline by fractionally distilling the cracked effluent to separate therefrom two particular individual streams, one portion containing predominantly hydrocarbons of four carbon atoms ($C_4$ stream) and the other predominantly hydrocarbons of five carbon atoms ($C_5$ stream) and etherifying only the tertiary olefins in the two portions containing predominantly four and five carbon atom hydrocarbons respectively, each of the two portions being etherified in a manner preferred for the predominant tertiary olefin in the portion. By this procedure, a cracked hydrocarbon stream containing a range of tertiary olefins which can be etherified is fractionated to provide a first portion containing predominantly $C_4$ hydrocarbons, a second portion containing predominantly $C_5$ hydrocarbons, and a remainder of which an appropriate part can be passed directly to a gasoline pool. The foregoing $C_4$ hydrocarbon portion containing isobutylene is then etherified with methanol in any of the known ways of etherifying such isobutylene-rich fractions, the conventional processes generally providing excellent conversions of isobutylene and yields of methyl tertiary butyl ether (MTBE). This ether has a high octane blending number and is a highly advantageous ingredient for addition to a gasoline pool. The entire etherified $C_4$ portion containing the ether can be blended directly into a gasoline pool, or more advantageously, the MTBE can be separated from the stream and added to a gasoline pool while the unreacted ingredients of the $C_4$ stream are diverted to other applications, for example an alkylation process for alkylate gasoline preparation. According to the present invention the predominantly $C_5$ hydrocarbon portion, separated from a cracked hydrocarbon effluent stream, boiling at atmospheric pressure in the range from 80° F. to 122° F. (27° C. to 50° C.), and containing the isomers 2-methyl butene-1 and 2-methyl butene-2, is etherified with methanol separately from the etherification of the $C_4$ fraction in a novel processing sequence by which optimum conversions of the foregoing isomers and optimum yields of tertiaryamyl methyl ether (TAME) are obtained. It may be noted in passing that the 3-methyl butene-1 isomer also is present in the $C_5$ hydrocarbon fraction but does not etherify to form TAME and is substantially inert under the reaction conditions in the present invention. It can also be noted that, although several alcohols may be used to etherify 2-methyl butenes, methanol is the most practicable, particularly from an economic standpoint, and therefore used in this disclosure as the only practicable primary alcohol for the process of this invention.

The development of the present invention was based upon observations that the reaction kinetics for the formation of TAME from methanol and methyl butenes are distinctly different from those for the formation of MTBE from methanol and isobutylene, so different in fact that the relevant reaction rate constants for TAME are found to be generally less than ten percent of the reaction rate constants for MTBE. This figure can be greater or less than ten percent depending on conversion level. This difference, which may reach nearly two orders of magnitude, warrants a major difference in the respective modes of preparation of the products. Because of the difference, the preparation of MTBE from stoichiometric proportions of isobutene and methanol by either batch or continuously operating prior art processes has readily achieved conversions between 85% and nearly 100% whereas, in work leading to the present invention, comparable preparations of TAME have been found to achieve conversions that have been at most 50% to 60%; these latter conversions could be achieved only with impracticably low space velocities, and with industrially practicable space velocities the conversions have been around 35%. An additional observation warranting the preparation of TAME from methanol and methyl butenes separately from preparation of higher methyl ethers, as well as separately from MTBE preparation, is that the higher methyl ethers, for example tertiaryhexyl methyl ethers, have octane blending numbers little or no better than that of olefinic hydrocarbon stock from which normally they are made. Hence there is no improvement in octane rating achieved by converting tertiary hexenes and higher tertiary olefins to methyl ethers for blending into gasoline; the etherification of 2-methyl butenes with methanol in presence of iso-hexenes and higher tertiary olefins wastes methanol when the etherification product is intended solely for blending into gasoline for octane improvement thereof, and a reduced 2-methyl butene etherification reaction rate is achieved due to the dilution effect. In sharp contrast, a typical $C_5$ fraction of cracked or pyrolysis gasoline, when the tertiary olefin content thereof is etherified in accordance with the present invention, undergoes an increase of substantially five in its Research and Motor octane numbers. This amount of octane appreciation is known to be real, based on carefully controlled measurements, whereas the octane appreciations reported in the art for tertiaryhexyl methyl ethers and tertiaryheptyl methyl ethers, prepared from $C_6$ and $C_7$ iso-olefin containing hydrocarbon fractions, are believed to be largely illusory due to the presence of readily formed peroxides in the olefinic fractions; the peroxides depress the octane number of the olefinic fractions but are destroyed during etherification of the tertiary olefins in the fractions, thus creating a false impression of significant improvement in octane number by etherification when in fact only little has occurred. The blending octane members in a typical commercial gasoline of some ethers and ether mixtures are listed in Table I for comparison.

TABLE I

| BLENDING OCTANE NUMBERS OF ETHERS | | |
|---|---|---|
| Ether | RON[1] | MON[2] |
| Methyl tertiarybutyl ether | 118 | 101 |
| Tertiaryamyl methyl ether | 112 | 99 |
| Tertiaryhexyl methyl ethers[3] | 100 | 90 |
| Tertiaryheptyl methyl ethers[3] | 90 | 77 |

[1] Research Octane Number
[2] Motor Octane Number
[3] Blends of ethers obtained by etherification with methanol of $C_6$ and $C_7$ olefinic hydrocarbon fractions respectively.

The present invention thus consists in a process for preparation of gasoline containing tertiaryamyl methyl ether (TAME) which comprises:

1. separating, from lower and higher boiling compounds, an olefinic hydrocarbon portion boiling at atmospheric pressure in the range from 80° F. to 122° F. (27° C. to 50° C.) and containing a mixture of hydrocarbons having predominantly five carbon atoms each, of which hydrocarbons at least 10% are 2-methyl butenes, 2. passing the olefinic hydrocarbon portion, together with methanol in a proportion of from 0.5 to 3.0 mols of methanol per mol 2-methyl butenes present, into contact with a bed of solid acidic etherifying catalyst in a reactor at temperature in the range from 150° F. to 240° F. (66° C. to 116° C.) under pressure sufficient to maintain the passing material in the liquid phase, said contact being of sufficient duration to etherify from 15% to 60% of the 2-methyl butenes in the passing material during said contact, 3. passing a proportion of the effluent stream from said reactor to a distillation column wherein said proportion of effluent is fractionally distilled under reflux and wherein a bottom fraction containing substantially all the ethers entering the column is withdrawn from the bottom of the column and a distillate fraction is withdrawn from the top of the column, 4. blending said ether containing bottom fraction and any remainder of the effluent stream passing directly from said reactor into a gasoline product, 5. recycling a proportion of the distillate fraction from the top of the column to the reactor for additional contact with said catalyst, and 6. passing a proportion of said distillate fraction into said gasoline product when the entire effluent stream from the reactor is passed to the distillation column.

In preferred embodiments of the invention, a proportion of from 10% to 85% of the effluent stream from the reactor is passed to the distillation column for fractional distillation, although this proportion can be as high as 100% of the effluent. When a proportion of 100% of the reactor effluent is passed to the distillation column, it becomes necessary to bleed off a proportion, for example from 20% to 30%, of the distillate from the column into gasoline product in order to prevent accumulation of volatile material in the system; when a significant proportion of the ether containing reactor effluent is withdrawn and blended directly into gasoline product, it is not necessary to bleed off any proportion of the distillate and the entire distillate is recycled to the reactor. The size of the preferred proportion of the effluent stream from the reactor to be passed to the distillation column depends largely on the extent to which it is desired to increase the conversion of 2-methyl butenes into TAME at the cost involved in recycling unreacted distillate through the reactor. To achieve the highest practicable conversions of 2-methyl butenes to TAME it is preferred to pass from 60% to 85% of the reactor effluent to the distillation column and pass the remainder directly to gasoline blending. When the cost (for example the steam cost) for distilling such high proportions of reactor effluent is not warranted for the incremental increase in conversion of 2-methyl butenes to TAME that is achieved by these higher proportions being recycled, it becomes preferred to pass a lower proportion of reactor effluent to the distillation column and withdraw a greater proportion of effluent for blending directly into gasoline. A noticeable increase in conversion is achieved by passing as little as 10% of the reactor effluent to the distillation column, but it is preferred to pass at least from 15% to 40% to the distillation column to achieve more recycle and obtain the highest economically feasible conversion of 2-methyl butenes to TAME; when operating costs (e.g. for steam) for the distillation are sufficiently low, it becomes preferred to pass a higher proportion, for example from 40% to 35% of the effluent to the distillation column, to obtain maximum possible conversion of 2-methyl butenes to TAME.

Throughout this specification and ensuing claims the percentages and proportions referred to are percentages and proportions by weight unless otherwise specifically indicated.

Figure 2:
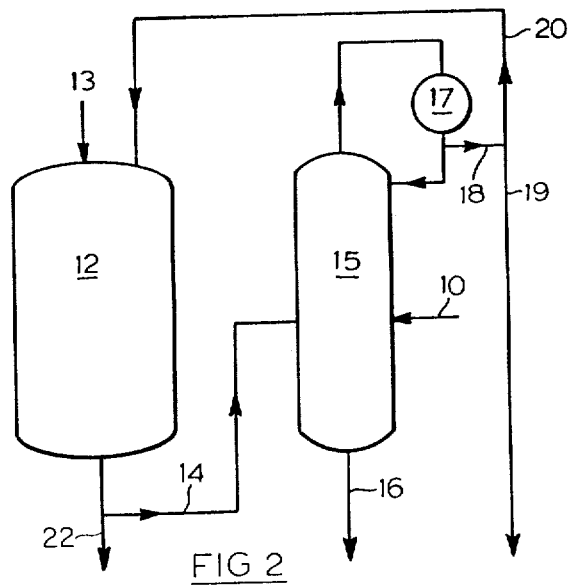

The invention may be more readily understood from the following description and by reference to the accompanying flow diagrams, FIGS. 1 and 2, showing two different suitable arrangements for conducting the process of the invention.

In FIG. 1, an olefinic hydrocarbon stream 10 is fed to a distillation column 11 in which it is fractionated to provide a predominantly C$_5$ hydrocarbon liquid distillate fraction boiling at atmospheric pressure in the range from 80° F. to 122° F. (27° C. to 50° C.) and containing at least 10% 2-methyl butenes. When the feed is LCCG and/or HPGB, heavier material withdrawn from the column can be fed to gasoline blending; alternative disposal can be used if desired or when other feed streams are used. The C$_5$ fraction is passed via line 21 to a catalyst containing etherification reactor 12 into which a supply of methanol is also fed via line 13, in proportion to the tertiary olefins in the total feed to the reactor. Effluent from the reactor 12, containing the ethers produced therein, passes via line 14 where its flow may be divided, with one proportion being withdrawn through a draw-off line 22 and blended into a gasoline product; the balance of the reactor effluent in line 14 passes to a second distillation column 15 in which it is fractionated to provide a bottom fraction containing the ethers in the second part of the effluent. The ether containing bottom fraction flows from the column via line 16 to be blended into gasoline product. Distillate from the column condenser 17 is separated from the reflux line via line 18 wherein it may be divided between line 19, which passes a proportion of the distillate to a gasoline product, and line 20, which recycles the remaining proportion of the distillate to the reactor 12. As indicated earlier, it is necessary to bleed off a proportion of the distillate, via line 19, when all of the reactor effluent is fed to the column, but generally it is more efficient to pass some of the reactor effluent, for example from 15% to 90% thereof, directly to gasoline product through line 22, thereby providing a bleed-off for volatile material and precluding any need for withdrawing distillate through line 19. In the most economic preferred embodiments of the invention when steam costs are high, from 60% to 85% of the reactor effluent is passed directly to gasoline product and correspondingly from 40% to 15% of it is passed to the distillation column for separation of a recycle portion as distillate. Similar proportions for recycle indicated for FIG. 1 are also suitable for FIG. 2.

In FIG. 2 there is shown a simplified modification of the foregoing process which permits operation with a single distillation column instead of two when the portion of the olefinic hydrocarbon feed stream 10 boiling above 122° F. (50° C.) is to be blended into gasoline product along with, hence diluted by, ethers formed in the process. In this modification an olefinic cracked gasoline fraction, for example LCCG or HPGB, is fed via line 10 into a fractional distillation column 15 which also fractionates at least a part of the effluent, flowing via line 14, from an etherification reactor 12. In column 15 a portion of the cracked gasoline, boiling at atmospheric pressure in the range from 80° F. to 122° F. (28° C. to 50° C.), is taken overhead in the column distillate while the higher boiling remainder of the cracked gasoline is withdrawn from the bottom of the column via line 16 as an ether containing residue to be blended into product gasoline. The column distillate withdrawn through line 18 can be divided between lines 19 and 20, with part going via line 19 to a gasoline product as bleed-off and the remainder going via line 20 as olefinic feed to the etherification reactor 12. Methanol is fed to the reactor via line 13. Etherification of tertiary olefins from line 20 with methanol from line 13 takes place in contact with etherification catalyst in reactor 12. The flow of ether containing effluent from reactor 12 can be divided into two parts, with one part being withdrawn through draw-off line 22 and blended into a gasoline product; the second part of the reactor effluent flows via line 14 to column 15 where it is fractionated, simultaneously with fractionation of the olefinic cracked gasoline feed, to discharge the ether content of the effluent from the column in the bottom fraction, along with higher boiling hydrocarbons of the cracked gasoline feed. The bottom fraction from column 15 is blended into gasoline product. As with the embodiment shown in FIG. 1, it is necessary to bleed off a proportion of the distillate, via line 19, when all of the reactor effluent is fed to the distillation column, but it is generally more efficient to withdraw some of the reactor effluent through line 22 for blending directly to gasoline product; this more efficient alternative generally precludes any need for withdrawing distillate through line 19.

In preferred embodiments of the invention the mol proportion of methanol per mol of 2-methyl butenes in the hydrocarbon feed stream is in the range from 0.7 to 1.5 and most preferably it is 0.9 to 1.1. More particularly, it is preferred that the proportion of methanol to 2-methyl butenes in the feed to the reactor be kept low enough that the proportion of methanol in the reactor effluent also is appropriately low, for example from 2% to 9%, and/or correspondingly the proportion of methanol in the distillation column bottom fraction, containing substantially all the ethers, is appropriately low, for example below 5%. The efficiency of the separation in the distillation column obviously affects the proportion of free methanol in the distillation bottom fraction.

The liquid hourly space velocity (LHSV) of the reactor feed in contact with catalyst in the process of this invention (and accordingly the contact time) is preferably adjusted to achieve etherification of from 25% to 50% of the 2-methyl butenes in the streams being fed to the reactor, most preferrably from 32% to 40%. Space velocities (LHSV) in the range from 1.5 to 4 are preferred. Pressure during the reaction must be sufficient to maintain the reactants in the liquid phase, and thus may vary with reaction temperature; generally from 5 to 10 atmospheres is adequate, and the desired LHSV is readily achieved. The preferred reaction temperature for etherification is in the range 165° F. to 225° F. (74° C. to 107° C.), most preferably 175° F. to 200° F. (79° C. to 94° C.). Below the preferred temperature range the etherification reaction is undesirably slow and above this range the selectivity of the reaction for the intended ether formation is undesirably reduced.

Solid acidic etherifying catalysts are well known in the art, and include the sulfonated, crosslinked, polystyrene ion-exchange resins in their acid form, for example "Dowex 50" (trademark), "Amberlyst 15" (trademark), "Ionac C-252" (trademark), "Rexyn 101(H)" (trademark) and "Nalcite HCR" (trademark). The foregoing commercial products are the preferred catalysts for the present invention. Other such etherifying catalysts suitable for the invention include the sulfonated phenol-formaldehyde resins, for example those sold under the names "Amberlite IR-1" (trademark), "Amberlite IR-100" (trademark) and "Nalcite MX" (trademark), and the zeolitic water softeners made by sulfonation of coals, for example those sold under the names "Zeo-Carb H" (trademark) and "Nalcite X" (trademark).

The following examples are given to illustrate the invention and some aspects thereof.

EXAMPLE 1

The effluent from a commercial catalytic cracking operation was separated as normal into a gaseous fraction containing most of the hydrocarbons of four or less carbon atoms, a liquid light catalytically cracked gasoline (LCCG) fraction containing predominantly hydrocarbons of from five to seven carbon atoms, and heavier liquid hydrocarbon fractions. The LCCG fraction then was further fractionated by distillation to isolate a fraction containing predominantly hydrocarbons of five carbon atoms ($C_5$ fraction) of which 25 percent was 2-methyl butene isomers; this $C_5$ fraction was also found to contain 5 percent of hydrocarbons of six or more carbon atoms, and the remainder of the LCCG fraction was found to contain 1 percent of hydrocarbons of only five carbon atoms. Etherification of the 2-methyl butenes in the $C_5$ fraction was carried out in a continuous flow tubular reactor packed with "Ionac C-252" (trademark) resin, a sulfonated crosslinked styrene/divinylbenzene polymeric ion exchange resin in the acid form. The $C_5$ fraction, a stream of methanol, and a recycle stream identified below were fed together into the reactor in proportions to provide a molar ratio of methanol to 2-methyl butenes in the reactor feed of 1.10; under steady operating conditions the concentration of 2-methyl butenes in the reactor feed was 15.7 percent by weight. Total flow to the reactor provided a liquid hourly space velocity (LHSV) of 2.0. Temperature of the liquid feed entering the reactor was around 191° F. (88° C.) and pressure therein was maintained around 14.5 atmospheres. Average temperature across the reactor during the exothermic reaction was 200° F. (94° C.). The entire effluent from the reactor was fed to the tenth plate from the top of a twenty-five plate distillation column equipped with a reboiler and operated at atmospheric pressure with a reflux ratio of 2. Reboiler temperature was maintained at 195° F. (90° C.) and column top temperature was maintained at 100° F. (39° C.). Under these conditions, 83.7 percent of the column feed was withdrawn from the top of the column and 16.3 percent of the feed was withdrawn in the bottom draw-off. The bottom draw-off from the distillation column, containing 53 percent TAME, 3 percent methanol, balance hydrocarbons including the $C_6$ and heavier hydrocarbons of the reactor feed and a portion of the less volatile $C_5$ hydrocarbons, included all the ether produced in the reactor and was withdrawn for blending into a gasoline pool. The top draw-off was divided into two streams, the first constituting 25 percent of the draw-off was withdrawn for blending into the gasoline pool and the remaining 75 percent of the top draw-off was recycled to the reactor, being the recycle stream previously referred to which was combined with $C_5$ fraction and fresh methanol as reactor feed. The top draw-off contained 89 percent of the methanol fed to the column, three-quarters of this 89 percent being returned to the reactor in the recycle stream, as stated above. The one-quarter of the top draw-off withdrawn for the gasoline pool contained a dynamic equilibrium proportion of the more volatile unreacted hydrocarbon components. Under the foregoing conditions of reaction, distillation, and recycle, the concentration of 2-methyl butenes in the total feed to the reactor was 15.7 percent. During each passage through the reactor, 36 percent of the 2-methyl butenes in the total reactor feed stream was converted to tertiaryamyl methyl ether (TAME) with a selectivity of substantially 100 percent. Overall conversion of 2-methyl butenes to TAME in the process was 70 percent; the 30 percent unconverted went to the gasoline pool via the top draw-off (about 24 percent) and bottom draw-off (about 6 percent) from the distillation column. The measured research octane number (RON) of the original $C_5$ hydrocarbon fraction was compared with the calculated RON of the product withdrawn for blending into the gasoline pool, based on the known blending octane number of TAME; the octane appreciation achieved by the etherification of the 2-methyl butene content of the $C_5$ fraction in the process was found to be 5.3 octane numbers (research).

EXAMPLE 2

This example was carried out in the same equipment used in Example 1 and using the same procedure, with the following exceptions: (1) the $C_5$ hydrocarbon fraction used contained 35.4 percent of 2-methyl butene isomers, (2) the molar ratio of methanol to 2-methyl butenes fed to the reactor was 0.99, and (3) the average temperature over the reactor was 165° F. (74° C.). With this lower average reaction temperature and higher concentration of reactive material in the feed, the conversion of 2-methyl butenes to TAME per pass through the reactor was only 29 percent (versus the 36 percent achieved in the previous Example), and the overall conversion to TAME and octane appreciation of the fraction were correspondingly less.

EXAMPLE 3

For this Example, a volume of light catalytically cracked gasoline (LCCG) was mixed with an equal volume of a partially hydrogenated pyrolysis gasoline fraction from steam cracking of naphtha, and the mixture fractionated to provide a $C_5$ fraction containing about 34 percent 2-methyl butenes. Again the etherification and subsequent distillation were carried out as in Example 1, except that the average temperature in the reactor was 194° F. (90° C.) and the LHSV in the reactor was 3.4; under these conditions the concentration of 2-methyl butene isomers in the overall feed to the reactor (including recycle portion) was 18 percent and the conversion of these isomers per pass through the reactor was 37.2 percent. The octane appreciation achieved by the etherification of the $C_5$ fraction was substantially the same as that achieved in Example 1.

EXAMPLE 4

An LCCG fraction isolated from a commercial catalytic cracking operation was further fractionated by distillation, similarly to that described in Example 1, to obtain a predominantly $C_5$ fraction of which 25 percent was 2-methyl butene isomers; the $C_5$ fraction also contained five percent of hydrocarbons of six or more carbon atoms and the remainder of the LCCG contained 6 percent of hydrocarbons of only five carbon atoms. Etherification of the 2-methyl butenes in the $C_5$ fraction was carried out in the same continuous flow tubular reactor containing "Ionac C-252" resin catalyst used in Example 1. Streams of the $C_5$ fraction, methanol, and recycle material identified below were fed together into the reactor in proportions to provide a molar ratio of methanol to 2-methyl butenes in the reactor feed of 0.95; under steady operating conditions the concentration of 2-methyl butenes in the reactor feed was 23.4 percent by weight. Total flow of streams into the reactor provided an LHSV of 2.8 therein. Temperature of the liquid feed entering the reactor was substantially 191° F. (88° C.) and pressure in the reactor was substantially 14.5 atmospheres. Average temperature across the reactor in which the exothermic etherification reaction occurred was 200° F. (94° C.). The effluent stream from the reactor was divided into two streams, the first, constituting 70 percent of the effluent, was withdrawn for blending directly into gasoline product and the second, being 30 percent of the effluent, was fed to the tenth plate from the top of a 25 plate distillation column. As in Example 1, this column was operated at atmospheric pressure with a reflux ratio of 2, a reboiler temperature of 195° F. (90° C.) and a column top temperature of 100° F. (38° C.). Under these conditions, 23.6 percent of the column feed was withdrawn as a bottom draw-off from the reboiler for blending into gasoline product and the remaining 76.4 percent of the column feed was withdrawn as a top draw-off from the reflux line. This top draw-off stream was returned as part of the feed to the reactor and constituted the recycle material referred to above. The bottom draw-off from the column included all the ether, 11 percent of the methanol, all the $C_6$ and heavier hydrocarbons, and a portion of the unreacted $C_5$ hydrocarbons fed to the column. The top draw-off from the column recycled to the reactor included 89 percent of the methanol and a portion of the unreacted $C_5$ hydrocarbons fed to the column. The 70 percent of the reactor effluent withdrawn for blending directly into the gasoline pool contained a dynamic equilibrium proportion of the more volatile unreacted hydrocarbon components, and accumulation of volatile components in the system thus was precluded. Under the foregoing conditions of reaction, distillation, draw-off and recycle, the concentration of 2-methyl butenes in the total feed to the reactor was 23.4 percent. During passage through the reactor, 36 percent of the 2-methyl butenes in the total reactor feed stream was converted to TAME with a selectivity of substantially 100 percent. Overall conversion of 2-methyl butenes to TAME in the process was 42 percent; the 58 percent unconverted went to gasoline product via the reactor effluent and bottom draw-off of the distillation column. Comparison of the measured RON of the original predominantly $C_5$ hydrocarbon fraction with the calculated RON of the material withdrawn for blending into gasoline product showed the octane appreciation achieved by the etherification to be 3.2 octane numbers (research). The 42 percent conversion achieved in this example was lower than that achieved in Example 1 by virtue of the much lower proportion of material being recycled. Nevertheless, continuous recycle of a proportion of 23 percent of the reactor effluent, i.e. of material that has already been subjected to reaction conditions, achieved a 16 percent increase in conversion over that achieved without recycling.

The preceding Examples 1 to 4 inclusive have illustrated embodiments of the invention with apparatus arranged as shown in FIG. 1 of the drawings. The following Example illustrates an embodiment of the invention with apparatus arranged as shown in FIG. 2 of the drawings.

EXAMPLE 5

In this Example, a 36 plate distillation column was utilized simultaneously to distill an LCCG fraction and part of the etherified effluent from the continuous flow tubular reactor used in Example 1. Flow of feed and product streams to, from, and between the reactor and distillation column were arranged as illustrated in FIG. 2. An LCCG hydrocarbon fraction was fed to the seventeenth plate from the top of the column, which was operated at a pressure of 6.8 atmospheres absolute, with a reflux ratio of 0.6, a reboiler temperature of 313° F. (156° C.) and a column top temperature of 205° F. (96° C.) a stream of effluent from the reactor simultaneously was fed, as a recycle stream, to the seventeenth plate from the top of the column. The LCCG fraction used had the same composition as that used in Example 4. Under the foregoing column operating conditions, 51.7 percent of the total feed to the column (i.e. the feed via lines 10 and 14 of FIG. 2) was withdrawn as a bottom draw-off from the reboiler for blending into product gasoline and the remaining 48.3 percent of the column feed was withdrawn as top draw-off from the reflux line. This top draw-off was all fed to the reactor simultaneously with a stream of methanol to provide a molar ratio of methanol to 2-methyl butenes in the total feed to the reactor of 0.95; under steady operating conditions the concentration of 2-methyl butenes in the reactor feed was 21 percent by weight. Total flow of streams into the reactor provided an LHSV therein of 1.5. Temperature of the liquid feed entering the reactor was 158° F. (70° C.) and pressure in the reactor was substantially 14.5 atmospheres. Average temperature across the reactor in which the etherification reaction occurred was 167° F. (75° C.). The effluent stream from the reactor was divided into two streams, the first, constituting 70 percent of the effluent, was withdrawn for blending directly into gasoline product and the second, being 30 percent of the effluent, was fed as the recycle stream to the seventeenth plate from the top of the distillation column, referred to above. The bottom draw-off from the column, which was 51.7 percent of the column feed as indicated above, included all the ether, 24 percent of the methanol, and 90 percent of the $C_6$ and heavier hydrocarbons as well as a small proportion of the $C_5$ hydrocarbons fed to the column. The top draw-off recycled to the reactor included 76 percent of the methanol and a major proportion of the $C_5$ hydrocarbons fed to the column. The 70 percent of the reactor effluent withdrawn for blending directly into gasoline product contained a dynamic equilibrium proportion of the more volatile unreacted components of the feed, and their accumulation in the system thus was precluded. Under the specified conditions of distillation, reaction, draw-off, and recycle, the concentration of 2-methyl butenes in the total reactor feed stream was 21.0 percent; during passage through the reactor this concentration was converted to TAME with a selectivity of substantially 100 percent. Overall conversion to TAME achieved was 40 percent. Comparison of the RON of the predominantly $C_5$ hydrocarbon portion of the LCCG with the calculated RON of the product material blended into gasoline product showed the octane appreciation achieved by the etherification to be 3.1 octane numbers (research).

Numerous modifications obviously can be made in the process illustrated by the foregoing examples without departing from the scope of this invention. Thus, any hydrocarbon stream of predominantly five carbon atom hydrocarbons with significant (10 percent or more) 2-methyl butene content can be reacted with methanol to form TAME and thereby enhance the octane rating of the stream. The contact times between the etherification catalyst and reactants (i.e. liquid hourly space velocities) and the temperatures in the reactor can be varied as necessary to achieve the etherification of an optimum proportion of the 2-methyl butenes, it being appreciated that extremely long contact time may be required to achieve conversion to equilibrium proportions of 2-methyl butenes and TAME at lower temperatures and that the equilibrium proportion of TAME is higher at the lower temperatures (as would be expected in an exothermic reaction). To increase the overall contact time without changing the LHSV in the reactor it is merely a matter of increasing the proportion of material that is recycled to the reactor, thereby also decreasing the proportion that is directed to the gasoline pool through bleed line 22 or line 19; at the same time the flow rate of $C_5$ fraction and fresh methanol feed to the process would be reduced correspondingly and a higher overall conversion of 2-methyl butenes to TAME would be achieved. Thus the proportion of material recycled can be varied as desired. The distillation can be operated at atmospheric or superatmospheric pressure as desired, and various heat-exchanging facilities can be provided to achieve or maintain the temperature conditions desired throughout the process. Under some conditions, for example when the gasoline pool into which the etherification products are blended is low in aromatics, it may be desirable to remove at least a portion of the methanol from any stream which goes to the gasoline pool, to reduce possibility of phase separation due to moisture in the gasoline pool. It is possible also to operate the process of the invention as illustrated in either FIG. 1 or 2 using withdrawal to gasoline product through both lines 19 and 22 simultaneously, but withdrawal through reactor effluent line 22 alone is preferred. When withdrawal through distillate draw-off line 19 alone is used, it is preferred to withdraw from 20 percent to 30 percent of the distillate to achieve maximum practicable yield of TAME by recycling 80 percent to 70 percent of the distillate, and when recycling costs are too high for economic operation with such proportions, lower proportions of from 70 percent down to 30 percent may be used for recycling.

Numerous other modifications in the various expedients described can be made without departing from the scope of the invention which is defined in the following claims.

What is claimed is:

1. Process for preparation of gasoline containing tertiaryamyl methyl ether which comprises
   1. separating, from lower and higher boiling compounds, an olefinic hydrocarbon portion boiling at atmospheric pressure in the range from 80° F. to 122° F. (27° C. to 50° C.) and containing a mixture of hydrocarbons having predominantly five carbon atoms each, of which hydrocarbons at least 10% are 2-methyl butenes,
   2. passing the olefinic hydrocarbon portion, together with methanol in a proportion of from 0.5 to 3.0 mols of methanol per mol 2-methyl butenes present, into contact with a bed of solid acidic etherifying catalyst in a reactor at temperature in the range from 150° F. to 240° F. (66° C. to 116° C.) under pressure sufficient to maintain the passing material in the liquid phase, said contact being of sufficient duration to etherify from 15% to 60% of the 2-methyl butenes in the passing material during said contact,
   3. passing a proportion of the effluent stream from said reactor to a distillation column wherein said proportion of effluent is fractionally distilled under reflux and wherein a bottom fraction containing substantially all the ethers entering the column is withdrawn from the bottom of the column and a distillate fraction is withdrawn from the top of the column,
   4. blending said ether containing bottom fraction and any remainder of the effluent stream passing directly from said reactor into a gasoline product,
   5. recycling a proportion of the distillate fraction from the top of the column to the reactor for additional contact with said catalyst, and
   6. passing a proportion of said distillate fraction into said gasoline product when the entire effluent stream from the reactor is passed to the distillation column.

2. A process as claimed in claim 1 in which the hydrocarbon portion boiling from 80° F. to 125° F. (27° C. to 52° C.) is a portion of a light catalytically cracked gasoline stream.

3. A process as claimed in claim 2 in which the molar proportion of methanol admixed with 2-methyl butenes in the reactor is in the range from 0.7 to 1.5.

4. A process as claimed in claim 3 in which the solid acidic etherifying catalyst is from the group consisting of sulfonated crosslinked polystyrene ion-exchange resins in the acid form, sulfonated phenol-formaldehyde resins, and sulfonated coals.

5. A process as claimed in claim 4 in which the reaction temperature is maintained in the range from 165° F. to 225° F. (74° C. to 107° C.).

6. A process as claimed in claim 5 in which the liquid hourly space velocity through the reactor is in the range from 1.5 to 4 and the proportion of 2-methyl butenes in the flow through the reactor which is etherified is in the range from 25% to 50%.

7. A process as claimed in claim 6, wherein the distillation column bottom draw-off fraction contains less than 5% methanol.

8. A process as claimed in claim 7 in which the entire effluent from the reactor is fed to the distillation column and the distillate from the distillation column is divided to provide a first portion of from 20% to 30% of the distillate for passing to a gasoline product and correspondingly from 80% to 70% of the distillate for recycle to the reactor for contact with etherifying catalyst.

9. A process as claimed in claim 1 in which the hydrocarbon portion boiling from 80° F. to 122° F. (27° C. to 50° C.) is a portion of a partially hydrogenated pyrolysis gasoline stream from a hydrocarbon steam cracking operation.

10. A process as claimed in claim 9 in which the molar proportion of methanol admixed with 2-methyl butenes in the reactor is controlled to maintain the proportion of methanol in the reactor effluent in the range from 2% to 9%.

11. A process as claimed in claim 10 in which the fractional distillation in the distillation column reduces the proportion of methanol in the bottom fraction to below 5%.

12. A process as claimed in claim 2 in which the olefinic hydrocarbon portion boiling at atmospheric pressure in the range from 80° F. to 122° F. (27° C. to 50° C.) is separated from the light catalytically cracked gasoline stream by fractionally distilling the stream alone to obtain the said olefinic portion as a distillate which is all fed to the reactor with methanol for contact with the etherifying catalyst.

13. A process as claimed in claim 9 in which the partially hydrogenated gasoline stream is fed to the same distillation column as the effluent stream from the reactor, and said gasoline stream is fractionally distilled therein to separate said olefinic hydrocarbon portion, boiling at atmospheric pressure in the range from 80° F. to 122° F. (27° C. to 50° C.), as distillate from higher boiling material withdrawn from the column in the bottom fraction.

14. A process as claimed in claim 1 in which a proportion of from 15% to 90% of the effluent stream from the reactor is passed directly into a gasoline product and correspondingly from 85% to 10% of the effluent stream is passed to the distillation column, with a proportion of 100% of the distillate fraction from the top of the column being recycled to the reactor.

15. A process as claimed in claim 14 in which the proportion of reactor effluent passed directly to gasoline product is in the range from 60% to 85%.

16. A process as claimed in claim 2 in which the light catalytically cracked gasoline stream is fed to the same distillation column as the effluent stream from the reactor and said gasoline stream is fractionally distilled therein to separate said olefinic hydrocarbon portion, boiling at atmospheric pressure in the range from 80° F. to 122° F. (27° C. to 50° C.) as distillate from higher boiling material withdrawn from the column in the bottom fraction.

* * * * *